(12) United States Patent
Jackson

(10) Patent No.: US 8,304,001 B1
(45) Date of Patent: Nov. 6, 2012

(54) PHS1

(75) Inventor: Christi Jeanaye Jackson, Chattanooga, TN (US)

(73) Assignee: Christi Jackson, Chattanooga, TN (US)

( * ) Notice: Subject to any disclaimer, the term of this patent is extended or adjusted under 35 U.S.C. 154(b) by 36 days.

(21) Appl. No.: 13/038,371

(22) Filed: Mar. 1, 2011

(51) Int. Cl.
*A61K 36/53* (2006.01)
*A61K 36/61* (2006.01)

(52) U.S. Cl. .......................... 424/742; 424/747; 424/725

(58) Field of Classification Search .......................... None
See application file for complete search history.

(56) References Cited

U.S. PATENT DOCUMENTS

2012/0039973 A1 * 2/2012 Grlica et al. .................. 424/405

OTHER PUBLICATIONS

Translation of CN 101233864 (2008).*

* cited by examiner

*Primary Examiner* — Susan Hoffman
(74) *Attorney, Agent, or Firm* — Christi Jackson

(57) ABSTRACT

This is a formula made up of 3.4% Eucalyptus oil [*Eucalyptus Globules*], 3.4% Peppermint oil [*Mentha x Piperita*], 3.4% Wintergreen oil [*Gaultheria Procumbens*], 3.4% Lavender oil [*Lavandula Angustifolia*], 1.7% Clove Bud oil [*Syzyguium aromaticum*] 60% glycerin, and 25% water. This invention is a topical muscle and joint pain reliever, as well as a decongestant.

3 Claims, No Drawings

PHS1

BACKGROUND OF THE INVENTION

This invention relates to topical analgesic medications and decongestants.

Many people suffer from chronic and acute pains that result from various causes. Joint and muscular pains can be frustrating as well as debilitating. Pain reduction is essential to a person's day to day life and wellbeing. Frequently taking NSAIDS or other prescription pain medications for chronic muscle or joint pain is not ideal, and options for natural topical pain relievers are especially limited.

Chest/nasal congestion is another health issue that a number of people suffer from. Most people use prescription drugs or over the counter medications, and there are not enough natural options for pain relief or congestion.

This invention creates a versatile and natural option for those suffering from one or more of the mentioned health issues.

SUMMARY OF THE INVENTION

This invention is multifunctional and easy to use. It is an analgesic that is applied topically. It also works as a decongestant when inhaled. It provides an alternative for individuals who may frequently take NSAIDS or other oral medications to alleviate their muscle and/or joint pain.

DETAILED DESCRIPTION OF THE INVENTION

This invention is a formulaic composition made up of approximately 3.4% Eucalyptus oil [*Eucalyptus Globules*], 3.4% Peppermint oil [*Mentha x Piperita*], 3.4% Wintergreen oil [*Gaultheria Procumbens*], 3.4% Lavender oil [*Lavandula Angustifolia*], 1.7% Clove Bud oil [*Syzygium aromaticum*], 60% Glycerin, and 25% water by volume. The active ingredients are all 100 percent pure therapeutic grade essential oils. The glycerin used in the formula is medical grade. The formula is made by pouring all of the ingredients together in a bottle. That allows the ingredients to mix and for the essential oils to be diluted. The formula is mixed together in a bottle, shaken up, and is then ready for use.

The active ingredients in the formula are essential oils, and they act as a topical analgesic, anti inflammatory, and decongestant.

This invention is made up of a composition that is diluted in order to be safe for topical use by applying solution to the afflicted area directly onto skin.

This solution can be administered as a topical spray for pain relief.

This solution can be used as a chest rub to relieve chest congestion.

This invention can also be used as a decongestant by pouring desired amount into a vaporizer.

This invention may also be used as a decongestant by applying desired amount to a cloth and inhaling it.

This invention can be bottled in dark colored plastic or dark colored glass bottle to preserve the solution.

The invention claimed is:

1. A topical analgesic formulaic composition, consisting of approximately 3.4% Eucalyptus oil, 3.4% Peppermint oil, 3.4% Wintergreen oil, 3.4% Lavender oil, 1.7% Clove Bud oil, 60% Glycerin, and 25% water by volume, will reduce discomfort associated with chronic or acute muscular and joint aches and pains when applied to skin.

2. Said formula in claim 1 also provides relief from nasal congestion when inhaled.

3. Said formula in claim 1 also relieves chest congestion when inhaled and/or applied to chest.

* * * * *